United States Patent [19]

Li

[11] Patent Number: 5,318,577
[45] Date of Patent: Jun. 7, 1994

[54] SUTURE THREADING DEVICE

[75] Inventor: Lehmann K. Li, Wellesley, Mass.

[73] Assignee: Mitek Surgical Products, Inc., Norwood, Mass.

[21] Appl. No.: 769,322

[22] Filed: Sep. 30, 1991

Related U.S. Application Data

[63] Continuation of Ser. No. 543,684, Jun. 26, 1990, abandoned.

[51] Int. Cl.$^5$ ............................................. A61B 17/00
[52] U.S. Cl. ................................................... 606/147
[58] Field of Search ................................. 606/144–147

[56] References Cited

U.S. PATENT DOCUMENTS

| 421,919 | 2/1890 | Fergen | 606/147 |
|---|---|---|---|
| 862,619 | 8/1907 | Driest | 606/147 |
| 2,336,689 | 12/1943 | Karle | 606/147 |
| 2,363,334 | 11/1944 | Jones | 606/147 |
| 2,439,383 | 4/1948 | Erickson | 606/146 |
| 3,139,089 | 6/1964 | Schwerin | 606/147 |
| 3,168,097 | 2/1965 | Dormia | 606/147 |
| 4,597,390 | 7/1986 | Mulhollan et al. | 606/147 |
| 4,614,187 | 9/1986 | Mulhollan et al. | 606/147 |

FOREIGN PATENT DOCUMENTS 528550 10/1940 United Kingdom ............... 606/147

Primary Examiner—Stephen C. Pellegrino
Assistant Examiner—Gary Jackson
Attorney, Agent, or Firm—Pandiscio & Pandiscio

[57] ABSTRACT

An improved suture threading apparatus is provided which includes an elongated rod having a handle at one of its ends and a needle holder adapted to receive the gripping end of a needle pivotally attached to its other end. The attachment is such that the needle holder may be moved by an actuator between a first position wherein a needle received by the needle holder is held substantially in alignment with the longitudinal axis of the elongated rod, and a second position wherein a needle received by the needle holder is held substantially transverse to the longitudinal axis of the rod. The actuator connects the needle holder to a finger grip substantially adjacent to the handle and includes biasing means which tend to hold the needle holder in its first position in the absence of a force applied to the finger grip overcoming the biasing force to move the needle holder to its second position. A method for using this apparatus to thread suture through tissue also is provided.

13 Claims, 8 Drawing Sheets

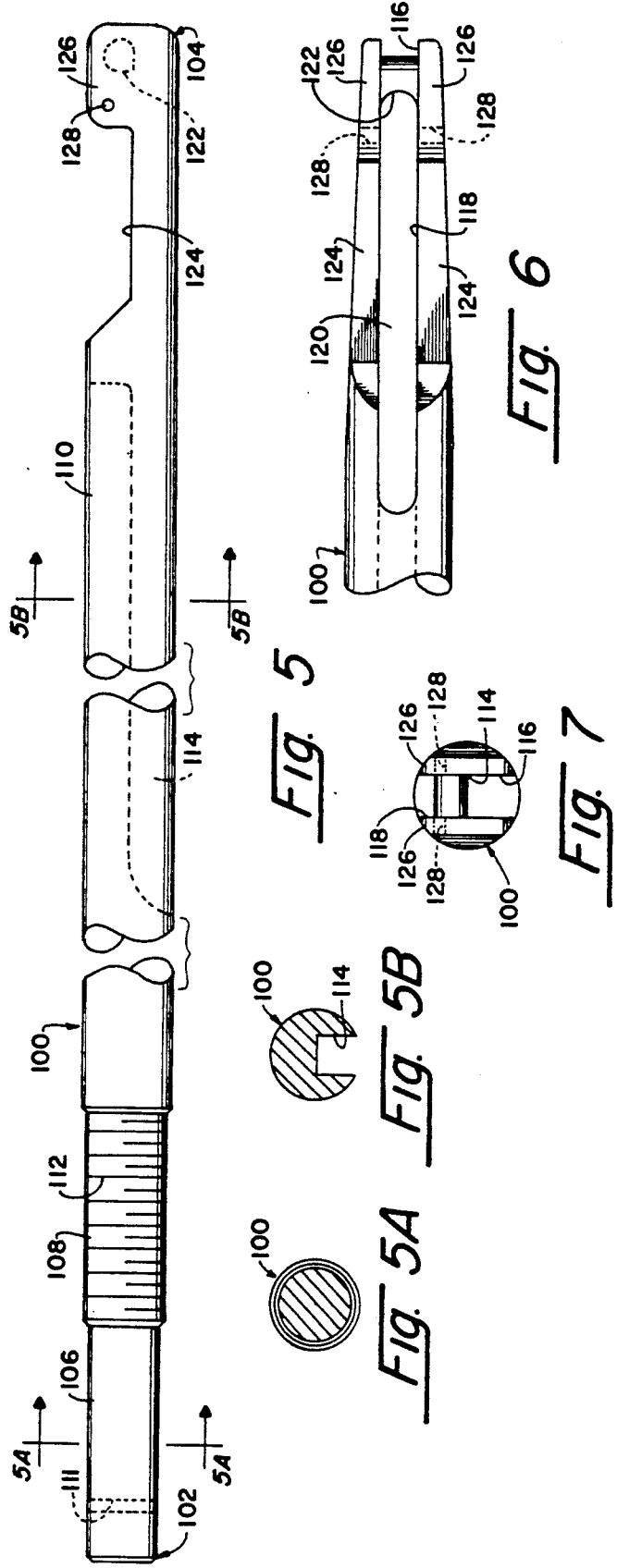

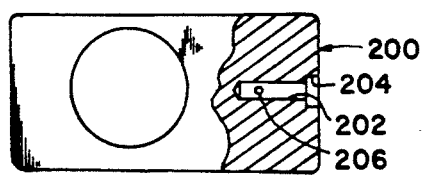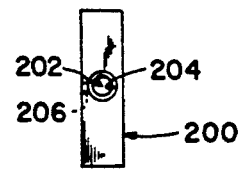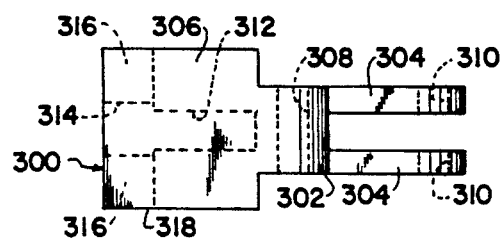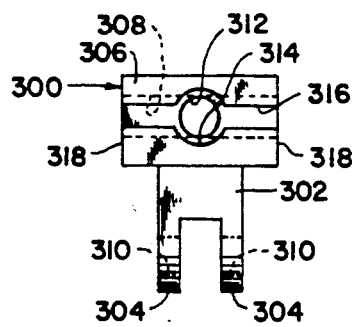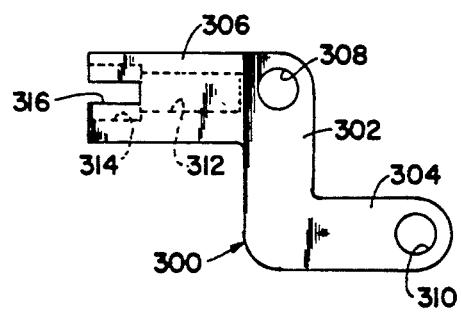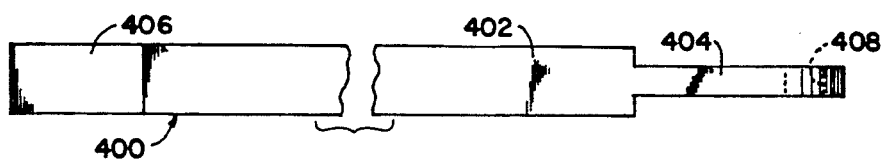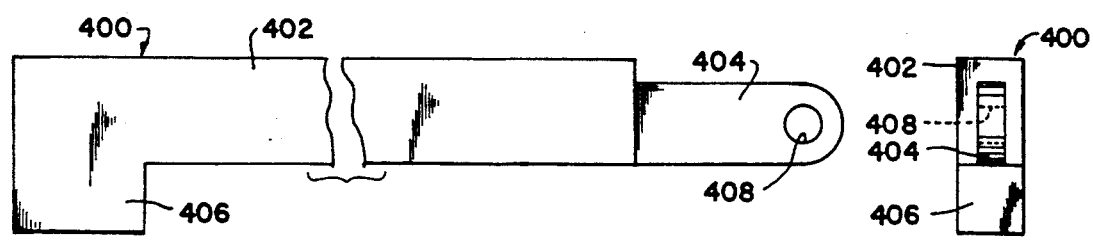

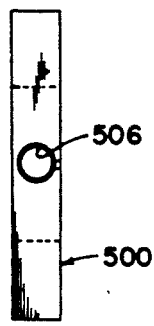
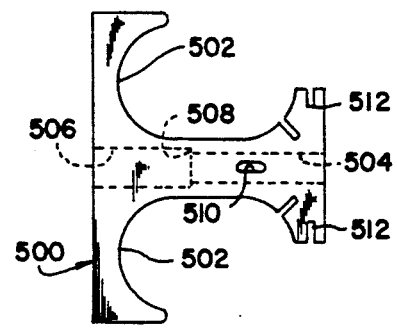
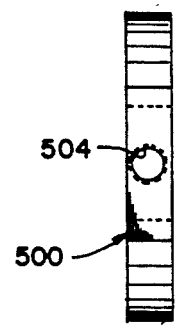
Fig. 17　　　Fig. 16　　　Fig. 18
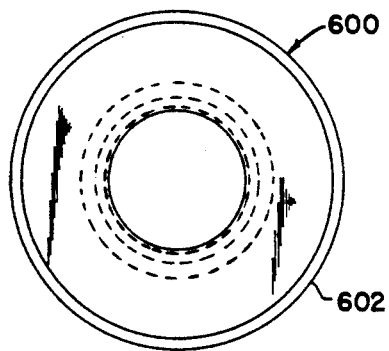
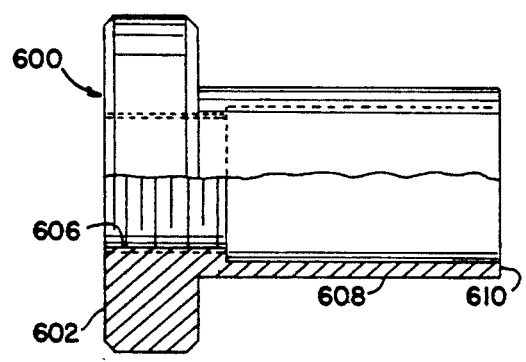
Fig. 20　　　Fig. 19
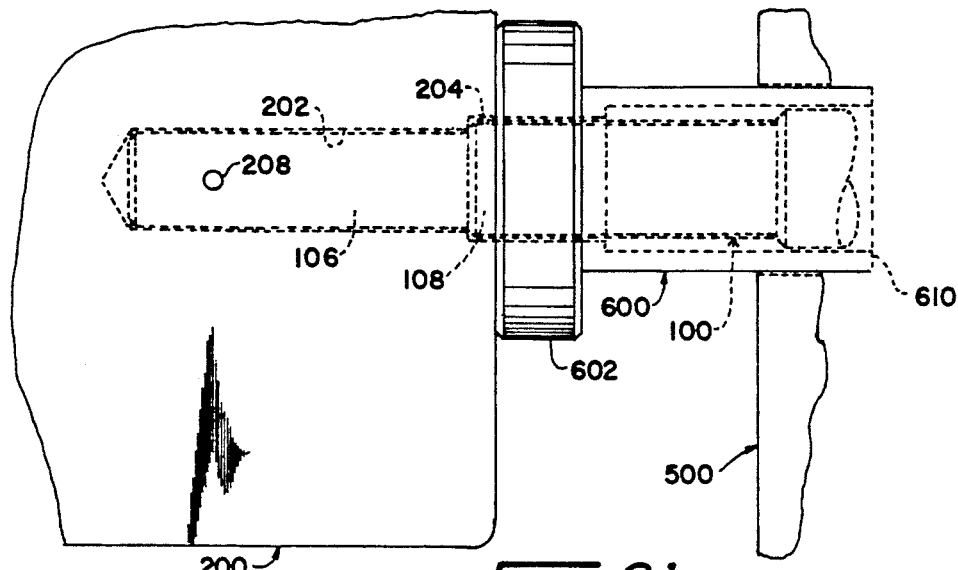
Fig. 21

SUTURE THREADING DEVICE

This is a continuation of copending application Ser. No. 07/543,684, filed on Jun. 26, 1990, now abandoned.

FIELD OF THE INVENTION

This invention relates to surgical instruments in general, and more particularly to surgical instruments for threading suture through tissue.

BACKGROUND OF THE INVENTION

Numerous surgical instruments have been developed for threading suture and surgical clips through and around tissue.

See, for example, U.S. Pat. Nos. 919,138 (Drake et al.), 1,037,864 (Carlson et al.), 1,449,087 (Bugbee), 1,635,066 (Wells), 1,815,725 (Pilling et al.) 1,822,330 (Ainslie), 1,856,721 (Nagelmann), 2,959,172 (Held), 3,013,559 (Thomas), 3,470,875 (Johnson), 3,840,017 (Violante), 3,842,840 (Schweizer), 3,901,244 (Schweizer), 3,946,740 (Bassett), 4,064,881 (Meredith), 4,164,225 (Johnson et al.), 4,169,476 (Hiltebrandt), 4,224,947 (Fukuda), 4,312,337 (Donohue), 4,493,323 (Albright et al.), 4,596,249 (Freda et al.), 4,602,635 (Mulhollan et al.), 4,621,640 (Mulhollan et al.), 4,633,869 (Schmieding), 4,643,178 (Nastari et al.) and 4,890,615 (Caspari et al.).

OBJECTS OF THE INVENTION

The principal object of the present invention is to provide a new and improved surgical instrument for threading suture through tissue.

Another object of the present invention is to provide a surgical instrument particularly well adapted to thread suture through tissue at a remote surgical site, wherein the remote surgical site must be accessed through a narrow cannula.

Still another object of the present invention is to provide a surgical instrument for threading suture through tissue which is relatively simple to manufacture and relatively easy to use.

Yet another object of the present invention is to provide a new method for threading suture through tissue.

SUMMARY OF THE INVENTION

These and other objects of the present invention are addressed by providing and using a new and improved suture threading device which comprises an elongated rod having a proximal end and a distal end and a longitudinal axis extending between the proximal end and the distal end, a handle fixed to the proximal end of the rod, a needle holder pivotally mounted to the distal end of the rod, the needle holder being adapted to receive the gripping end of a needle and present the penetrating end of the same needle, the needle holder being pivotally mounted to the distal end of the rod so that the needle holder can move between a first position wherein the needle is aligned with the longitudinal axis of the rod and a second position wherein the needle is transverse to the longitudinal axis of the rod, and actuating means for moving the needle holder between its first and second positions.

The actuating means comprises a finger grip slidingly mounted on the elongated rod and adapted to move toward and away from the distal end of the rod, biasing means for yieldably biasing the finger grip toward the distal end of the rod, and an actuator connecting the finger grip with the needle holder, whereby the needle holder will be forced into its aforementioned first position when the finger grip is biased towards the distal end of the rod (and away from the proximal end of the rod) by the biasing means, and the needle holder will be forced into its aforementioned second position when the finger grip is urged toward the proximal end of the rod (and away from the distal end of the rod) against the power of the biasing means.

BRIEF DESCRIPTION OF THE DRAWINGS

Still other objects and features of the present invention will be further disclosed or rendered obvious by the following detailed description of the invention, which is to be considered together with the accompanying drawings wherein:

FIG. 4 is a bottom view of the bottom side of the same suture threading device, the suture threading device having been rotated 90 degrees from the position shown in FIG. 3, with certain parts being shown in phantom;

FIG. 5 is a side view of the device's elongated rod;

FIG. 5A is a sectional view taken along line 5A—5A of FIG. 5;

FIG. 5B is a sectional view taken along line 5B—5B of FIG. 5;

FIG. 6 is a partial top view showing the top side of the front end of the same rod;

FIG. 7 is a front view showing the front end of the same rod;

FIG. 8 is a side view, partially in section, of the device's handle;

FIG. 9 is a front view of the same handle;

FIG. 10 is a side view of the device's needle

FIG. 11 is a rear view of the same needle holder;

FIG. 12 is a top view of the same needle holder;

FIG. 13 is a side view of the device's actuator;

FIG. 14 is a bottom view of the same actuator;

FIG. 15 is a front view of the same actuator;

FIG. 16 is a bottom view of the device's finger grip;

FIG. 17 is an end view of the rear end of the same finger grip;

FIG. 18 is an end view of the front end of the same finger grip;

FIG. 19 is a side view, partially cut away, of a nut which forms part of the device's biasing means;

FIG. 20 is an end view of the rear end of the same nut;

FIG. 21 is an enlarged, partial view showing the interconnection between the device's rod, handle, nut and finger grip in greater detail;

DETAILED DESCRIPTION OF THE INVENTION

Figure 1:
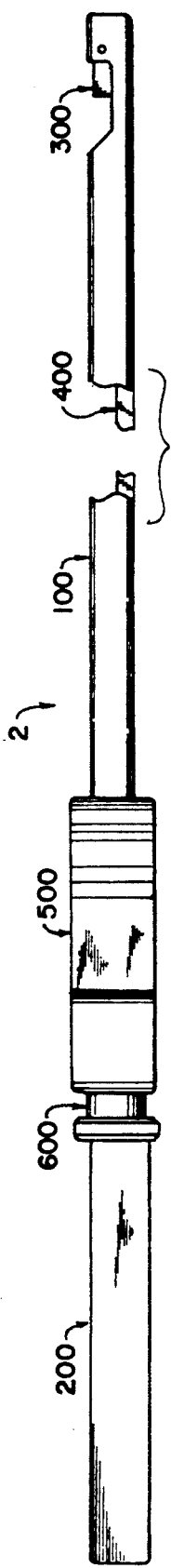
FIG. 1 is a side view of the right side of the suture threading device which comprises the present invention.
Figure 2:
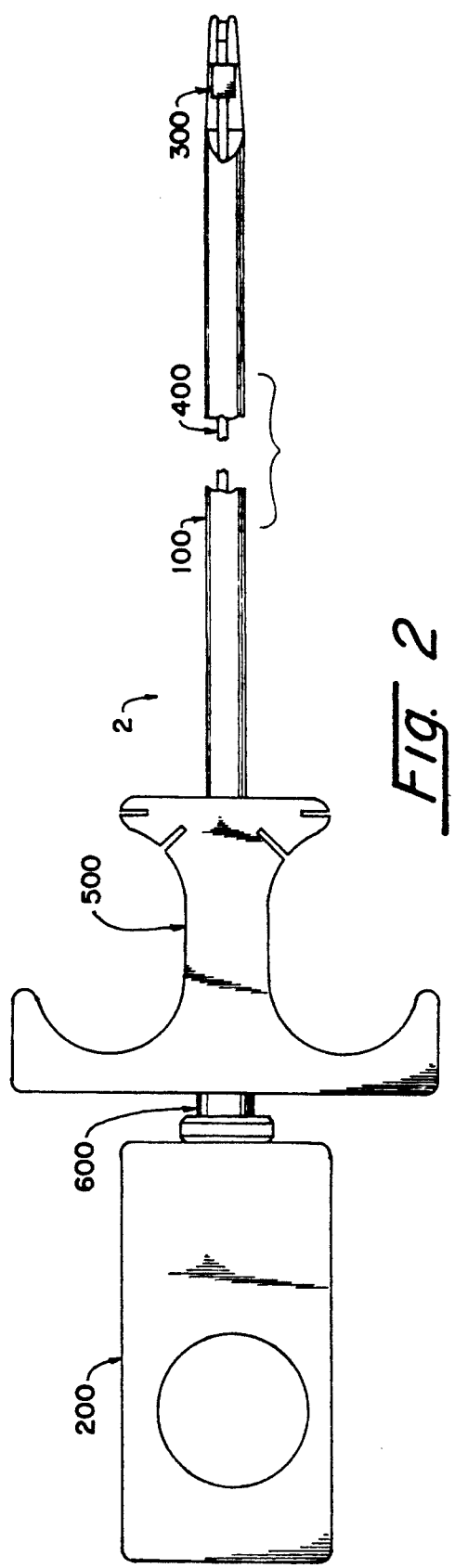
FIG. 2 is a top view of the top side of the same suture threading device, the suture threading device having been rotated 90 degrees from the position shown in FIG. 1.
Figure 3:
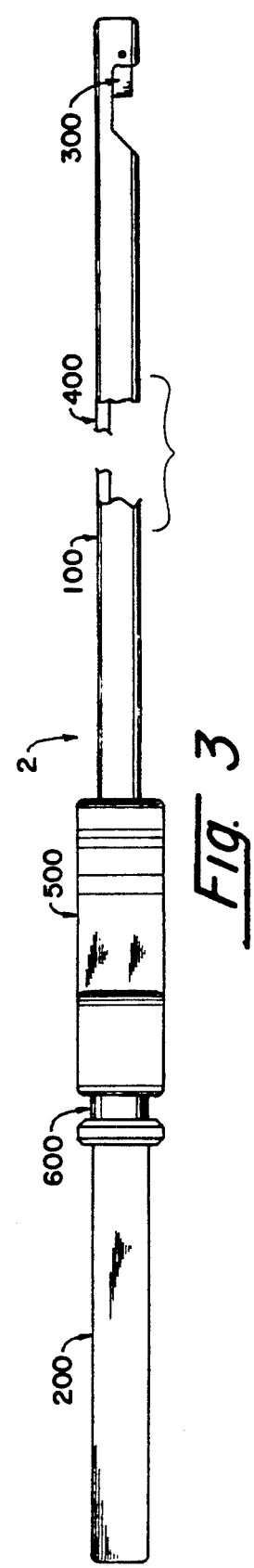
FIG. 3 is a side view of the left side of the same suture threading device, the suture threading device having been rotated 90 degrees from the position shown in FIG. 2.

Looking first at FIGS. 1-4, there is shown a suture threading device 2 which comprises the preferred embodiment of the present invention.

Suture threading device 2 generally comprises a rod 100, a handle 200, a needle holder 300, an actuator 400, a finger grip 500, and biasing means 600.

Rod 100 is shown in greater detail in FIGS. 5, 5A, 5B, 6 and 7. Rod 100 generally comprises a proximal end 102 and a distal end 104 (FIG. 5). More specifically, rod 100 comprises a first section 106, a second section 108, and a third section 110.

First section 106 has a solid, cylindrical configuration of a first diameter. First section 106 includes a bore 111 passing completely through the cylindrical section. Bore 111 is used to attach rod 100 to handle 200 as will hereinafter be described in further detail.

Second section 108 has a solid, cylindrical configuration of a second, larger diameter. Second section 108 also includes screw threads 112 on its outer surface. Screw threads 112 are used to attach rod 100 to nut 602, as will hereinafter be described in further detail.

Third section 110 has a generally cylindrical configuration of a third, even larger diameter. Third section 110 is cut away on its bottom side so as to form a bottom channel 114 (FIGS. 5 and 7), is cut away on its front side so as to form a front channel 116 (FIGS. 6 and 7), and is cut away on its top side so as to form a top channel 118 (FIGS. 6 and 7). Bottom channel 114 communicates with front channel 116, and front channel 116 communicates with top channel 118. Top channel 118 also communicates directly with bottom channel 114 for a portion of its length so as to form an elongated throughhole or slot 120 extending completely through rod 100 (FIG. 6). Slot 120 terminates in a front surface 122. The upper surface of third section 110 is also cut down somewhat, rearward of slot front surface 122, so as to form a pair of surfaces 124 (FIGS. 5 and 6). The foregoing construction provides a pair of upraised walls 126 at the front end of rod 100, separated by top channel 118 (FIGS. 5, 6 and 7). A bore 128 passes through upraised walls 126. Bore 128 is used to attach needle holder 300 to rod 100, as will hereinafter be described in further detail.

Handle 200 is affixed to the proximal end of rod 100. As seen in greater detail in FIGS. 8, 9 and 21, handle 200 includes a bore 202 sized to accommodate first section 106 of rod 100 and a counterbore 204 sized to accommodate second section 108 of rod 100. Handle 200 also includes a bore 206 which, when rod 100 is properly seated in handle 200, aligns with bore 111 in rod 100, whereby the handle may be pinned to rod 100 by a pin 208 (FIG. 21) and the two members thereby made fast to one another.

It is to be appreciated that when rod 100 and handle 200 are fastened together in the foregoing manner, they effectively form a skeleton or body to which the remaining members of the suture threading device attach.

Needle holder 300 is shown in greater detail in FIGS. 10-12. Needle holder 300 is adapted to receive the gripping end of a straight needle and to present the penetrating end of the same needle, as will hereinafter be described in further detail. Needle holder 300 is pivotally mounted to the distal end of rod 100 so that the needle holder can move between a first position wherein the needle is aligned with the longitudinal axis of the rod and a second position wherein the needle is transverse to the longitudinal axis of the rod. More particularly, needle holder 300 comprises a vertical riser 302 which is connected on its lower end to a pair of flanges 304 and which is connected on its upper end to a needle mount 306. Vertical riser 302 includes a bore 308 passing horizontally therethrough. Bore 308 is used to attach needle holder 300 to rod 100, as will hereinafter be described in further detail. Flanges 304 include a bore 310 passing horizontally therethrough. Bore 310 is used to attach needle holder 300 to actuator 400, as will hereinafter be described in further detail. Needle mount 306 includes a bore 312 and a counterbore 314. Bore 312 and counterbore 314 serve to receive the gripping end of a needle and present the penetrating end of the same needle, as will be hereinafter described in further detail. Slots 316 pass inward from mount side walls 318 to communicate with counterbore 314. Slots 316 serve to accommodate suture, as will hereinafter be described in further detail.

Needle holder 300 is adapted to be pivotally mounted to rod 100 by aligning needle holder hole 308 with rod hole 128 (FIG. 24), and then fitting a pin 320 (FIG. 23) through the aligned holes so as to pivotally mount the needle holder 300 to the rod 100. In this way, needle holder 300 is mounted to rod 100 such that the needle holder can move between (1) a first position wherein a needle 700 mounted in needle holder bore 312 and needle holder counterbore 314 is aligned with the longitudinal axis of the rod (FIGS. 23 and 24), and (2) a second position wherein the needle is transverse to the longitudinal axis of the rod (e.g., FIGS. 27 and 28), as will hereinafter be described in further detail.

Actuating means are provided for moving the needle holder 300 between its aforementioned first and second positions. These actuating means comprise the actuator 400 which has one of its ends connected to the needle holder 300 for moving the needle holder about at the distal end of rod 100, the finger grip 500 slidingly mounted on rod 100 and connected to the other end of actuator 400 for causing actuator 400 to move needle holder 300 about as desired, and the biasing means 600 for yieldably biasing finger grip 500 toward the distal end of rod 100 whereby needle holder 300 will be biased into its aforementioned first position.

Figure 23:
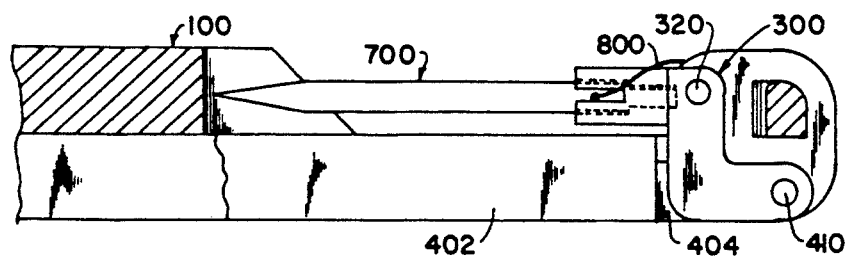
FIG. 23 is an enlarged side view showing the interconnection between the rod, needle holder and actuator in greater detail.
Figure 25:
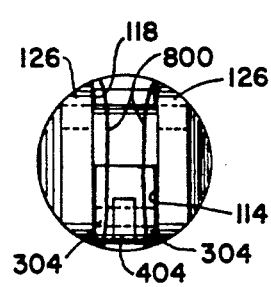
FIG. 25 is an enlarged front view showing the interconnection between the rod, needle holder and actuator in greater detail.
Figure 27:
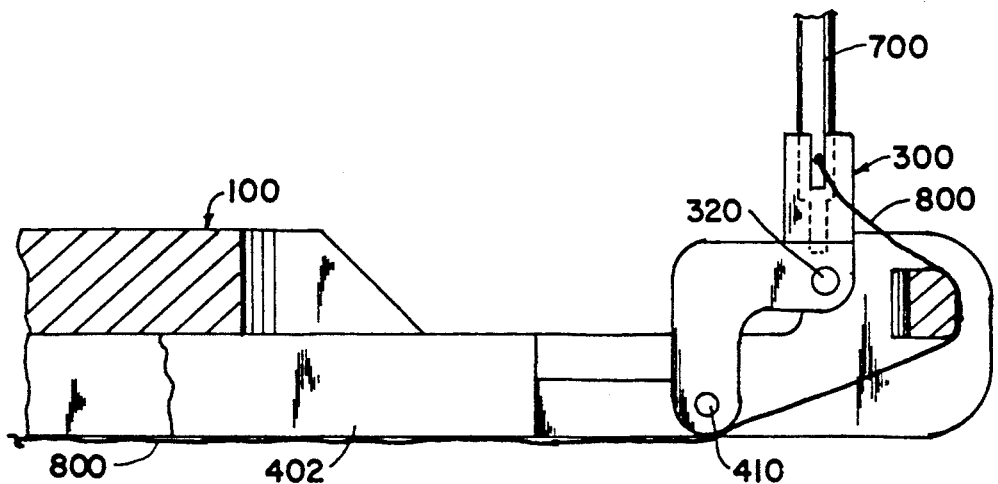
FIG. 27 is an enlarged side view showing the interconnection between the rod, needle holder and actuator in greater detail.
Figures 29A, 29B, 29C:
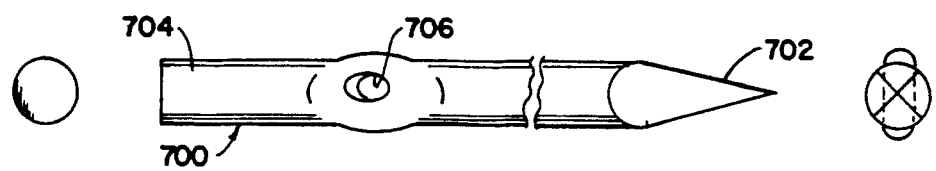
FIGS. 29A-29L, there are shown right end, side and left end views of showing a plurality of different needles which may be used in conjunction with the suture threading device.
Figures 29D, 29E, 29F:
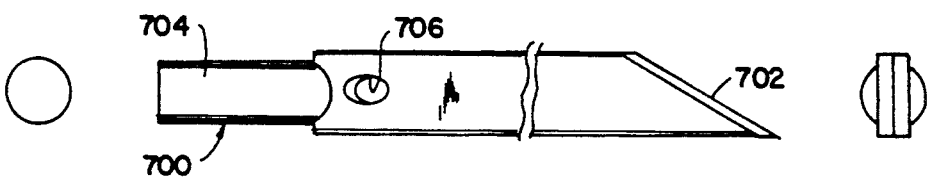
Figures 29G, 29H, 29I:
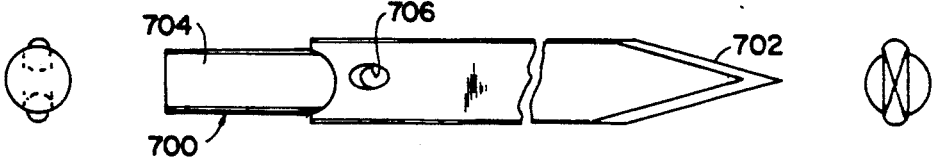
Figures 29J, 29K, 29L:
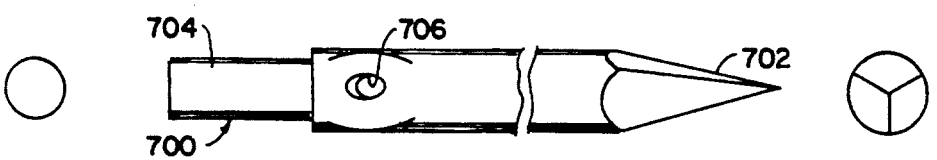

More specifically, and looking now at FIGS. 13-15, actuator 400 comprises a central section 402 terminating on its front end in flange 404 and on its rear end in a downward projection 406. A hole 408 is formed in front flange 404. Actuator 400 is sized such that central section 402 may be received within and make an easy sliding fit within bottom channel 114 of rod 100 (FIGS. 23, 25 and 27). The front end of actuator 400 is movably pinned to needle holder 300 by passing the actuator's front flange 404 between needle holder flanges 304, aligning actuator hole 408 with needle holder hole 310, and then pinning them together with a pin 410 (FIGS. 23, 25 and 27).

Figure 28:
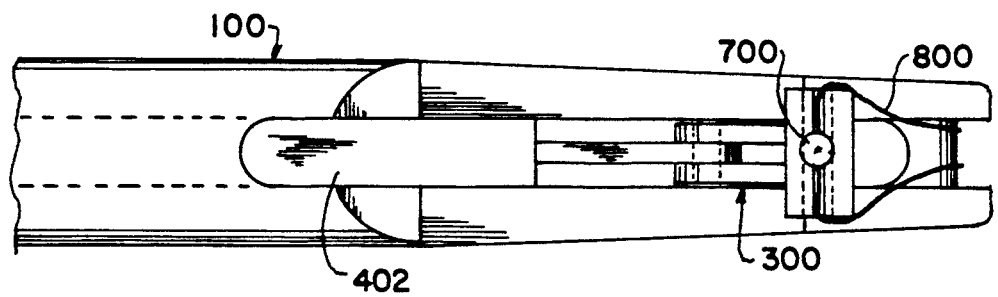
FIG. 28 is an enlarged top view showing the interconnection between the rod, needle holder and actuator in greater detail.

As a result of the foregoing construction, inasmuch as needle holder 300 is movably pinned to rod 100 by the pin 320 and inasmuch as needle holder 300 is movably pinned to actuator 400 by rod 410, it will be seen that by moving actuator 400 forward and backward within rod channel 114, needle holder 300 may be moved between a first position wherein its bore 312 and counterbore 314 are aligned with the longitudinal axis of the rod (FIGS. 23 and 24), and a second position wherein its bore 312 and counterbore 314 are perpendicular to the longitudinal axis of the rod (FIGS. 27 and 28). It will be appreciated that as the needle holder passes between these two positions, it will pass through an intermediate position such as that shown in FIG. 26.

Finger grip 500 and biasing means 600 are used to move the proximal end of actuator 400 about so as to cause the distal end of actuator 400 (and hence needle holder 300) to assume the desired position. Looking next at FIGS. 16, 17 and 18, finger grip 500 comprises a generally T-shaped member defining a pair of finger rests 502. A bore 504 opens on the front end of grip 500; a counterbore 506 opens on the rear end of grip 500. Bore 504 and counterbore 506 are coaxial with, and communicate with, one another. A shoulder 508 is formed at the intersection of bore 504 with counterbore 506. Bore 504 is sized to slidingly receive rod 100 as will hereinafter be described, and counterbore 506 is sized to slidingly receive a portion of a nut 602, as will also be hereinafter described. A slot 510 intersects bore 504 and opens on the finger grip's back surface. Slot 510 is sized to receive actuator projection 406, as will hereinafter be described in further detail. Finger grip 500 also includes a plurality of suture slots 512 for releasably holding suture to finger grip 500. To this end, suture slots 512 are sized so as to be approximately as wide as the diameter of an uncompressed piece of suture.

Finger grip 500 is mounted on rod 100 by passing rod 100 through the finger grip's bore 504 and counterbore 506. As noted above, bore 504 and counterbore 506 are sized so that finger grip 500 will be free to slide back and forth along the rod. At the same time, finger grip 500 is also securely attached to actuator 400 by fitting actuator projection 406 into finger grip slot 510 and making it fast. On account of the foregoing construction, it will be seen that when finger grip 500 is slid forward towards the distal end of rod 100 and away from handle 200, actuator 400 will have its front flange 404 moved forward toward the distal end of rod 100, whereby needle holder 300 will assume its aforementioned first position as seen in FIGS. 23 and 24, and when finger grip 500 is slid backward towards handle 200 and away from the distal end of rod 100, actuator 400 will have its front flange 404 moved backward away from the distal end of rod 100, whereby needle holder 300 will assume its aforementioned second position as seen in FIGS. 27 and 28.

Figure 22:
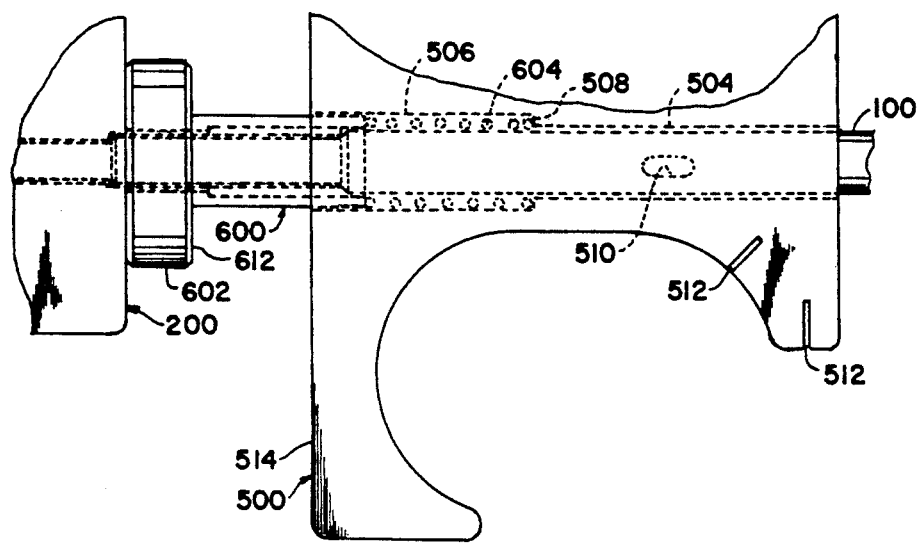
FIG. 22 is an enlarged, partial view also showing the interconnection between the device's rod, handle, nut and finger grip in greater detail.
Figure 24:
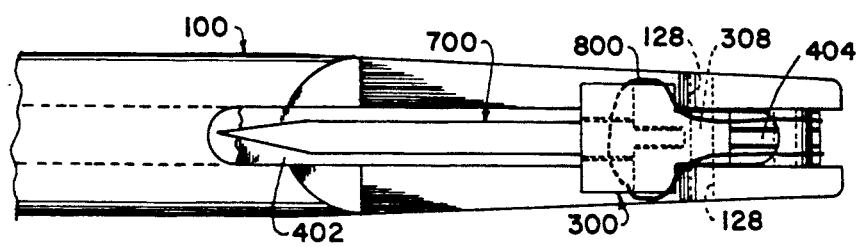
FIG. 24 is an enlarged top view showing the interconnection between the rod, needle holder and actuator in greater detail.

Biasing means 600 serves to bias finger grip 500 toward the distal end of rod 100, and hence needle holder 300 into its aforementioned first position as seen in FIGS. 23 and 24. More particularly, and looking now at FIGS. 19, 20, 21 and 22, biasing means 600 comprises a nut 602 and a spring 604. Nut 602 comprises a threaded bore 606 which is sized to ride on threads 112 of rod 100, and a sleeve 608 which is sized to slidingly fit within counterbore 506 of finger grip 500. Sleeve 608 terminates in an annular front surface 610. Spring 604 is captivated between the nut's annular end surface 610 and the finger grip's shoulder 508 (FIG. 22).

On account of the foregoing construction, it will be seen that spring 604 acts to normally bias finger grip shoulder 508 away from sleeve end surface 608. Inasmuch as nut 602 is attached to rod 100 by virtue of the engagement of threaded nut bore 606 with rod threads 112, and inasmuch as actuator 400 is attached to finger grip 500 by virtue of the engagement of actuator bottom projection 406 in finger grip slot 510, spring 604 has the effect of biasing the distal end of actuator 400 forward relative to handle 200, whereby needle holder 300 will be forced to assume its aforementioned first position as shown in FIGS. 23 and 24, wherein the needle holder's bore 312 and counterbore 314 are aligned with the longitudinal axis of the rod.

However, it will be appreciated that when a user engages the suture threading device 2 and applies rearward pressure to finger rests 502 so as to force the finger grip 500 rearward towards handle 200, the bias of spring 604 can be overcome so that finger grip 500 moves rearward relative to handle 200. As noted previously, inasmuch as the proximal end of rod 100 is fixed to handle 200 and inasmuch as the proximal end of actuator 400 is fixed to finger grip 500, this rearward movement of finger grip 500 relative to handle 200 has the effect of moving the distal end of actuator 400 rearward relative to handle 200, whereby needle holder 300 will be forced to assume its aforementioned second position as shown in FIGS. 27 and 28 wherein the needle holder's bore 312 and counterbore 314 are transverse to the longitudinal axis of the rod.

The various parts of the suture threading device 2 are sized and positioned such that when rear surface 514 of finger grip 500 (FIG. 22) engages nut surface 612 (FIG. 22) and thereby limits further rearward movement of finger grip 500 relative to rod 100, needle holder 300 will normally be in the position shown in FIGS. 27 and 28, i.e., the needle holder's bore 312 and counterbore 314 will extend perpendicular to the longitudinal axis of rod 100.

Looking next at FIGS. 29A-29L, there are shown right end, side and left end view of a variety of straight needles 700 which may be used in conjunction with suture threading device 2. Needles 700 are all characterized by a front penetrating point 702, a rear gripping end 704, and a suture receiving hole 706. Needles 700 are sized such that their gripping ends 704 may be slidingly received in needle holder bore 312 and counterbore 314, with the needles' penetrating points 702 exposed, and with the suture receiving holes 706 aligned with needle holder slots 316, in the manner shown in FIG. 23.

Suture threading device 2 is used as follows.

Figure 30A:
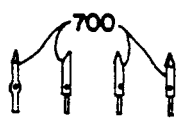
FIGS. 30a-30p are a series of views showing how the present invention may be used to thread suture through tissue at a remote surgical site.

As indicated in FIG. 30A, a needle 700 is first selected.

Figure 30B:
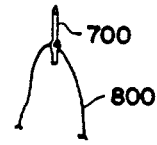

Next, as indicated in FIG. 30B, a piece of suture 800 is threaded through needle hole 706.

Figure 30C:
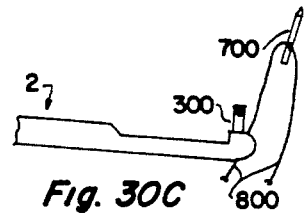

Then, as indicated in FIG. 30C, the suture threading device 2 is opened by pulling backward on finger grip 500, whereby the needle holder 300 will assume its aforementioned second position wherein the needle holder's bore 312 and counterbore 314 are positioned transverse to the longitudinal axis of the rod (FIGS. 27 and 28).

Figure 30D:
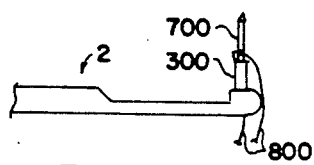

Next, as indicated in FIG. 30D, needle 700 is inserted into needle holder 300 so that gripping end 704 of the needle is seated securely in needle holder 300 and the penetrating point 702 of the needle is presented from the needle holder. Suture 800 is slipped through needle holder slots 316 so as to exit from the sides of needle holder 300.

Figure 30E:
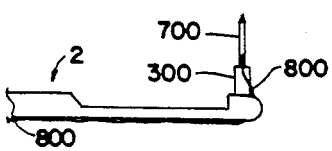

Then, as indicated in FIG. 30E, suture 800 is pulled into front slot 116 rod 100 and then into bottom slot 114 of rod 100. Suture 800 is kept under light tension at this point. Such light tension will held keep the needle 700 seated in needle holder 300, as well as held keep the suture in front slot 116 and bottom slot 114. See FIGS. 27 and 28.

Figure 30F:
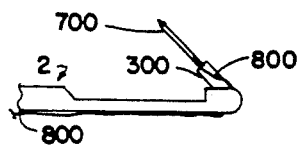

Next, as indicated in FIG. 30F, with tension maintained on the free ends of suture 800, the suture threading device 2 is closed by allowing spring 604 to force finger grip 500 forward toward needle holder 300 and away from handle 200. This causes needle 700 to be seated within top slot 118 of rod 100 so that the needle's penetrating point 702 is contained within and shielded by the boundaries of rod 100. The free ends of suture 800 are then secured to the suture threading device 2 under slight tension by wrapping the rear ends of suture 800 into one or more of suture slots 512 in finger grip 500. See FIGS. 23, 24 and 25.

Figure 30G:
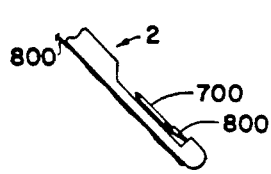

Thereafter, as indicated in FIG. 30G, the distal end of suture threading device 2 is passed through a cannula to the surgical site where the suture is to be passed through a piece of tissue.

Figure 30H:
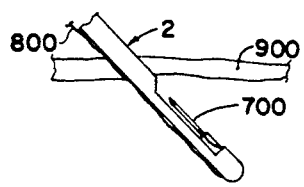

Next, as indicated in FIG. 30H, the distal end of suture threading device 2 is passed by the tissue 900 which is to have the suture threaded therethrough.

Figure 26:
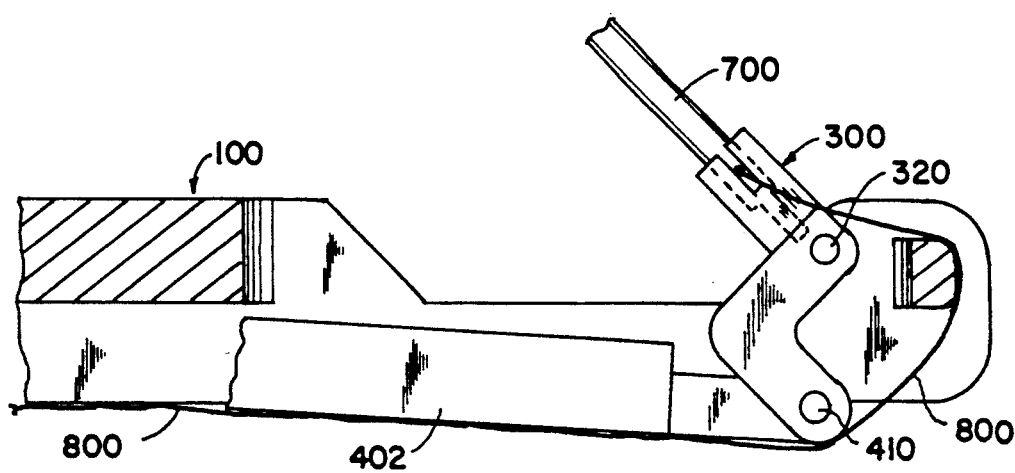
FIG. 26 is an enlarged side view showing the interconnection between the rod, needle holder and actuator in greater detail.
Figure 30I:
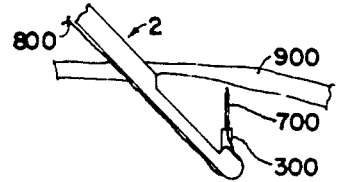

Once this has been done, the suture threading device is opened, as indicated in FIG. 30I, by pulling back on finger grip 500 so that needle holder 300 sits somewhere between its first and second positions, such as that shown in FIG. 26, with the penetrating point 702 of needle 700 positioned next to the tissue 900 which is to be sutured.

Figure 30J:
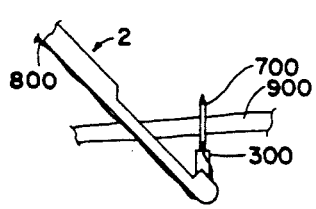

Next, as indicated in FIG. 30J, the suture threading device 2 is then pulled backward against tissue 900, whereby the penetrating point 72 of needle 700 will be forced through the tissue.

Figure 30K:
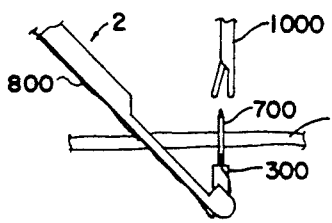
Figure 30L:
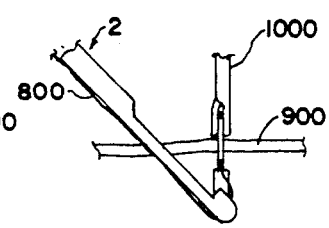

Thereafter, as indicated in FIGS. 30K and 30L, a needle gripping device 1000 of the sort well known in the art (e.g. a long-nosed forceps) is used to grip the portion of needle 700 penetrating tissue 900.

Figure 30M:
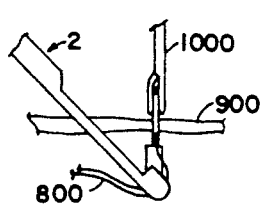

Then, as indicated in FIG. 30M, the suture 800 is released from finger grip 500 by disengaging it from suture slots 512.

Figure 30N:
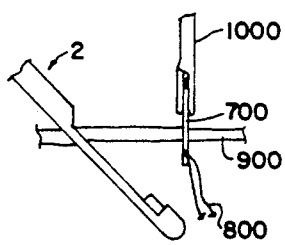
Figure 30O:
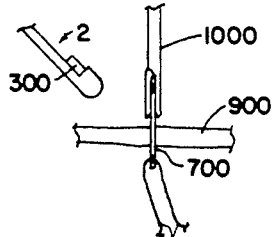

Thereafter, as indicated in FIG. 30N, the suture threading device 2 is disengaged from needle 700, and the suture threading device 2 is closed by allowing finger grip 500 to slip forward under the influence of spring 506, whereby the needle holder 300 will return to the position indicated in FIGS. 23 and 24.

Figure 30P:
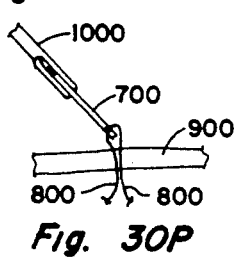

Finally, as indicated in FIG. 30P, gripping device 1000 is used to pull needle 700 completely through the tissue, whereby the suture 800 is threaded through the tissue. It will be appreciated that by using straight needles 700 in conjunction with suture threading device 2, gripping device 1000 can make a straight-forward retraction of the needle 700 through tissue 900.

As noted previously, nut 602 is normally mounted on rod 100 such that needle holder 300 will be in the position shown in FIGS. 27 and 28 (i.e., with the needle holder's bore 312 and counterbore 314 extending perpendicular to the longitudinal axis of rod 100) when finger grip rear surface 514 engages nut surface 612 and thereby limits further rearward movement of the finger grip 500 relative to rod 100. However, in view of the fact that nut 602 is adjustably mounted to rod 100 by virtue of the engagement between the nut's threaded bore 606 and the rod's threads 112, it will be seen that nut 602 may be positioned further forward on rod 100 if desired so as to limit the travel of needle holder 300 on rod 100 to a point short of that shown in FIGS. 27 and 28. By way of example, nut 602 may be positioned on rod 100 such that finger grip rear surface 514 engages nut surface 612 (and thereby limits further rearward movement of finger grip 500 relative to rod 100) when needle holder 300 is in the position shown in FIG. 26. Alternatively, the various parts of tool 2 may be sized and positioned such that the travel of needle holder 300 may extend to a point beyond that shown in FIGS. 27 and 28 when finger grip rear surface 514 engages nut surface 612.

Thus, it will be seen that nut 602 forms a movable stop which permits the user to precisely set the limit of the needle holder's movement relative to rod 100, i.e., nut 602 forms a movable stop which allows the user to precisely set the aforementioned second position of needle holder 300. Furthermore, it will be appreciated that inasmuch as the travel of needle holder 300 may be preset by proper positioning of nut 602 on rod 100 before the suture threading tool is inserted into the body, the user can be confident of always knowing the precise position of needle 700 relative to tool 2 once the suture threading tool 2 has been inserted into the body and finger grip 500 brought into engagement with nut 602. Such knowledge of the position of needle 700 relative to suture threading tool 2 can assist in located needle 700 with needle gripping device 1000.

Advantages of the Invention

Numerous advantages are achieved by using the present invention.

For one thing, the present invention provides a new and improved surgical instrument for threading suture through tissue.

For another thing, the present invention provides a surgical instrument particularly well adapted to thread suture through tissue at a remote surgical site, wherein the remote surgical site must be accessed through a narrow cannula.

The present invention also provides a surgical instrument for threading suture through tissue which is relatively simple to manufacture and relatively easy to use.

In addition, the present invention also provides a new method for threading suture through tissue.

What is claimed is:

1. A suture threading device comprising:
   an elongated rod having a proximal end and a distal end, and a longitudinal axis extending between said proximal end and said distal end;
   needle holder means for receiving the gripping end of a needle and presenting the penetrating end of the same needle, said needle holder means being pivotally mounted to said distal end of said rod so that said needle holder means is movable between (1) a first position wherein a needle received by said needle holder means is aligned with the longitudinal axis of said rod, and (2) a second position wherein a needle received by said needle holder means is transverse to said longitudinal axis of said rod; and actuating means for moving said needle holder means between its said first and second positions, wherein said needle holder means comprises a needle holder pivotally connected to said distal end of said rod, said needle holder having a bore and a counterbore, said bore being coaxial with and continuous with said counterbore, and further wherein the gripping end of a needle received by said needle holder means is received by said bore and said counterbore.

2. A suture threading device according to claim 1 wherein said needle holder further comprises at least one slot communicating with said counterbore, said at least one slot being sized and positioned to accommodate a suture attached to a needle received by said bore and said counterbore.

3. A suture threading device according to claim 1 wherein said needle holder means is pivotally connected to said distal end of said rod so that a needle received by said needle holder means will be oriented toward said proximal end of said rod when said needle holder means is in its said first position.

4. A suture threading device according to claim 1 wherein said rod defines an open cavity substantially adjacent to its said distal end, and further wherein said needle holder means is pivotally connected to said distal end of said rod so that a needle received by said needle holder means will be located within said open cavity when said needle holder means is in its said first position.

5. A method for threading suture through a piece of tissue having a far side and a near side so that the suture enters the tissue on the far side and exits the tissue on the near side, said method comprising the steps of:
(1) providing a suture threading device comprising:
  an elongated rod having a proximal end and a distal end, and a longitudinal axis extending between said proximal end and said distal end;
  needle holder means for receiving the gripping end of a needle and presenting the penetrating end of the same needle, said needle holder means being pivotally mounted to said distal end of said rod so that said needle holder means is movable between (1) a first position wherein a needle received by said needle holder means is oriented toward said proximal end of said rod and aligned with the longitudinal axis of said rod; and means is transverse to said longitudinal axis of said rod; and
  actuating means for moving said needle holder means between its said first and second positions;
and providing a needle having a gripping end and a penetrating end, said needle being mounted in said needle holder means so that said gripping end of said needle is received by said needle holder means and said penetrating end of said needle is presented by said needle holder means; and
providing a suture, said suture being attached to said needle;

(2) positioning said needle holder means in said first position so that said penetrating end of said needle is aligned with the longitudinal axis of said rod;
(3) advancing said suture threading device relative to said tissue so that said needle holder means is positioned adjacent said far side of said tissue;
positioning said needle holder means in a selected position between said first position and said second position so that said penetrating end of said needle is presented to said far side of said tissue;
(5) withdrawing said suture threading device relative to said tissue so that said penetrating end of said needle is forced to enter said far side of said tissue, pass through said tissue and exit said near side of said tissue, with said needle holder means remaining on said far side of said tissue;
(6) securing said penetrating end of said needle on said near side of said tissue so that said needle is maintained in position relative to said tissue;
(7advancing said suture threading device relative to said tissue so that said needle is withdrawn from said needle holder means, and
(8) pulling said needle completely through said tissue so that said suture extends through said tissue, and positioning said needle holder means in said first position, and withdrawing said suture threading device from a position adjacent said tissue.

6. A method according to claim 5 wherein said rod defines an open cavity substantially adjacent to its distal end, and further wherein said needle holder means is pivotally mounted to said distal end of said rod so that a needle received by said needle holder means will be located within said open cavity when said needle holder means is in its said first position.

7. A suture threading device comprising:
  an elongated rod having a proximal end and a distal end, and a longitudinal axis extending between said proximal end and said distal end;
  needle holder means for receiving the gripping end of a needle and presenting the penetrating end of the same needle, said needle holder means being pivotally mounted to said distal end of said rod so that said needle holder means is movable between (1) a first position wherein a needle received by said needle holder means is aligned with the longitudinal axis of said rod, and (2) a second position wherein a needle received by said needle holder means is transverse to said longitudinal axis of said rod; and
  actuating means for moving said needle means between its said first and second positions,
  wherein said actuating means comprises:
  a finger grip slidingly mounted on said elongated rod and adapted to move toward and away from said distal end of said rod;
  biasing means for yieldably biasing said finger grip toward said distal end of said rod; and
  an actuator connecting said finger grip with said needle holder means, whereby said needle holder means will be moved into its said first position when said finger grip is moved towards said distal end of said rod by said biasing means, and said needle holder means will be moved into its said second position when said finger grip is moved toward said proximal end of said rod against the power of said biasing means.

8. A suture threading device according to claim 7 wherein said actuator comprises a distal end and a proximal end, and further wherein said distal end of said actuator is pivotally connected to said needle holder means, and said proximal end of said actuator is secured to said finger grip.

9. A suture threading device according to claim 7 wherein said rod comprises suture retaining means for retaining a suture relative to said rod, and said finger grip comprises suture attaching means for attaching a suture to said finger grip, said suture retaining means being positioned on said rod and said suture attaching means being positioned on said finger grip so that when a suture is attached to a needle and the needle is received by said bore and said counterbore, and when the suture is positioned in said suture, retaining means and attached to said suture attaching means, the suture will help keep the needle positioned in said bore and said counterbore.

10. A suture threading device according to claim 7 wherein said needle holder means is pivotally mounted to said distal end of said rod so that a needle received by said needle holder means will be oriented toward said proximal end of said rod when said needle holder means is in its said first position.

11. A suture threading device according to claim 7 wherein said rod defines an open cavity substantially adjacent to its distal end, and further wherein said needle holder means is pivotally mounted to said distal end of said rod so that a needle received by said needle holder means will be located within said open cavity when said needle holder means is in its said first position.

12. A suture threading device comprising:
   an elongated rod having a proximal end and a distal end, and a longitudinal axis extending between said proximal end and said distal end, said rod defining an open cavity substantially adjacent to said distal end;
   needle holder means for receiving the gripping end of a needle and presenting the penetrating end of the same needle, said needle holder means being pivotally mounted to said distal end of said rod so that said needle holder means is movable between (1) a first position wherein said open cavity and aligned with the longitudinal axis of said rod, and (2) a second position wherein a needle received by said needle holder means is transverse to said longitudinal axis of said rod, said needle holder means defining an opening therein adapted to receive the gripping end of a needle; and
   mechanical actuating means for moving said needle holder means between its said first and second positions.

13. A suture threading device according to claim 12 wherein said needle holder means is pivotally mounted to said distal end of said rod so that a needle received by said needle holder means will be oriented toward said proximal end of said rod when said needle holder means is in its said first position.

* * * * *